US008497302B2

(12) United States Patent
Lorquin

(10) Patent No.: US 8,497,302 B2
(45) Date of Patent: Jul. 30, 2013

(54) MICROBIOLOGICAL METHOD FOR SYNTHESIZING CINNAMOYL AMIDE DERIVATIVES OF AMINO ACIDS

(75) Inventor: Jean Lorquin, Le Beausset (FR)

(73) Assignee: Institut de Recherche pour le Development, Marseille cedex (FR)

( * ) Notice: Subject to any disclaimer, the term of this patent is extended or adjusted under 35 U.S.C. 154(b) by 96 days.

(21) Appl. No.: 12/996,946

(22) PCT Filed: Jun. 5, 2009

(86) PCT No.: PCT/FR2009/000662
§ 371 (c)(1),
(2), (4) Date: Mar. 1, 2011

(87) PCT Pub. No.: WO2010/000964
PCT Pub. Date: Jan. 7, 2010

(65) Prior Publication Data
US 2012/0142778 A1 Jun. 7, 2012

(30) Foreign Application Priority Data

Jun. 9, 2008 (FR) ..................................... 08 03188

(51) Int. Cl.
*A61K 31/195* (2006.01)
*C07C 229/00* (2006.01)
(52) U.S. Cl.
USPC .......................................... 514/563; 562/444
(58) Field of Classification Search
USPC .......................................... 514/563; 562/444
See application file for complete search history.

(56) References Cited

U.S. PATENT DOCUMENTS 5,212,158 A 5/1993 Fiez Vandai

FOREIGN PATENT DOCUMENTS

| JP | 2003192522 | 7/2003 |
| JP | 2004175778 | 6/2004 |
| JP | 2006052150 | 2/2006 |
| JP | 2006052152 | 2/2006 |
| JP | 2006067870 | 3/2006 |

OTHER PUBLICATIONS

Ishihara et al. CAS: 143: 460142, 2005.*
Wang et al. CAS: 145: 249468, 2005.*
Anderson et al. 141: 157473, 2004.*
Horino et al. CAS: 135: 166835.*
Phillips et al. CAS: 132: 334380, 2000.*
Anai et al., Cinnamic Acid Derivatives as Tyrosinase Inhibitors and Antioxidants, and their uses; Database Accession No. 2004: 507814.
Iizuka et al., "Vasorelaxant Activity of N-Caffeoylamino Acids," *Yakugaku Zasshi*, 2003, pp. 963-971, vol. 123, No. 11.
Kato et al., "Preparation of Amides of Dihydroferulic Acid with L-alpha.—Amino Acid and their uses as Antioxidants and Tyrosinase Inhibitors" Database Accession No. 2006:166841.

Kato et al., "Preparation of N- (carboxyalkyl) Dihydoferulamides and their uses as Antioxidants and Tyrosinase Inhibitors," Database Accession No. 2006:169901.
Kim et al., "Anticholesterolemic Effect of 3,4-di-(OH)-phenylpropionic Amides in High-Cholesterol Fed Rats" *Toxicology and Applied Parmacology* 2005 pp. 29-36.
Knowles et al. "Desulfonylation of Amides Using Tributyltin Hydride, Samarium Diiodide or Zinc/Titanium Tetrachloride. A Comparison of Methods" *Tetrahedron* 56, 2000, pp. 979-988.
Lee et al., "Synthesis of Cinnamic Acid Derivatives and Their Inhibitory Effects on LDL-Oxidation, Acyl-CoA:cholesterol Acyltransferase-1 and-2 Activity, and Decrease of HDL-Particle Size," *Bioorganic & Medicinal Chemistry Letters*, 2004, pp. 4677-4681, vol. 14.
Lee et al. "Caffeoylglycolic and Caffeoylamino Acid derivatives, Halfmers of L-chicoric Acid, as new HIV-1 Integrase Inhibitors" *Science Direct* 2007, pp. 1309-1315.
Lee et al., "Hydroxylated Hydrocinnamides as Hypocholesterolemic Agents" *Bull. Korean Chem. Soc.* 2007 vol. 28 No. 10 pp. 1787.
Mimoto et al., "Rational Design and Synthesis of a Novel Class of Active Site-Targeted HIV Protease Inhibitors Containing a Hydroxymethylcarbonyl Isostere. Use of Phenylnorstatine or Allophenylnorstatine as a Transition-State Mimic" *Chem. Pharm. Bull* 1991 vol. 39 No. 9 pp. 2465-2467.
Nakanishi et al., "A novel Aminoacylase from Streptomyces Mobaraensis that efficiently catalyzes hydrolysis/Synthesis of N-acyl-L-amino Acids and N-acyl-peptides" Database Accession No. 2006:236619.
Sakakura et al., "Molybdenum Oxides as Highly Effective Dehydrative Cyclization Catalysts for the Synthesis of Oxazolines and Thiazolines" *Organic Letters* 2005 vol. 7 No. 10 pp. 1971-1974.
Song et al., "N-Acylamino Acids from *Ephedra distachya* Cultures" *Phytochemistry*,1992 vol. 31 No. 3 pp. 823-826.
Song et al., "*p*-Coumaroylamino Acids from Yeast-Elicited *Ephedra distachya* Cultures," *Arch. Pharm. Res.*, vol. 17, N. 1, pp. 51-53, 1994.
Song "Exogenous D-Ala Enhances the Accumulation of p-Coumaroylamino Acids in *Ephedra distachya* Cultures" *Arch. Pharm. Res.* 1995, vol. 18 No. 5 pp. 336-339.
Stark et al., "Isolation, Structure Determination, Synthesis, and Sensory Activity of *N*-Phenylpropenoyl-L-Amino Acids From Cocoa (*Theobroma cacao*)," *J. Agric. Food Chem.*, 2005, pp. 5419-5428, vol. 53.
Stark et al., "Quantitative Analysis of *N*-Phenylpropenoyl-L-Amino Acids in Roasted Coffee and Cocoa Powder by Means of a Stable Isotope Dilution Assay," *J.Agric. Food Chem.* 2006, pp. 2859-2867, vol. 54.
Tada et al., "Synthetic Search for Cosmetic Ingredients: Preparations, Tyrosinase Inhibitory and Antioxidant Activities of Caffeic Amides," *J Oleo Sci.*, 2002, pp. 19-27, vol. 51, No. 1.

(Continued)

*Primary Examiner* — Rei-tsang Shiao
(74) *Attorney, Agent, or Firm* — Womble Carlyle Sandridge & Rice, LLP

(57) ABSTRACT

Method for the microbiological production of cinnamoyl amide derivatives of amino acids, certain products that result therefrom and uses thereof, especially as antioxidants.

10 Claims, 1 Drawing Sheet

OTHER PUBLICATIONS

Tada et al., Compositions Containing Caffeic Acid Amides for Skin-Lightening Cosmetics and Topical Preparations Database Accession No. 2003: 525333.

Tu et al. "Novel Aminopeptidase N inhibitors Derived from 1,3,4-thiadiazole scaffold" *Bioorganic & Medicinal Chemistry* 2008, pp. 6663-6668.

* cited by examiner

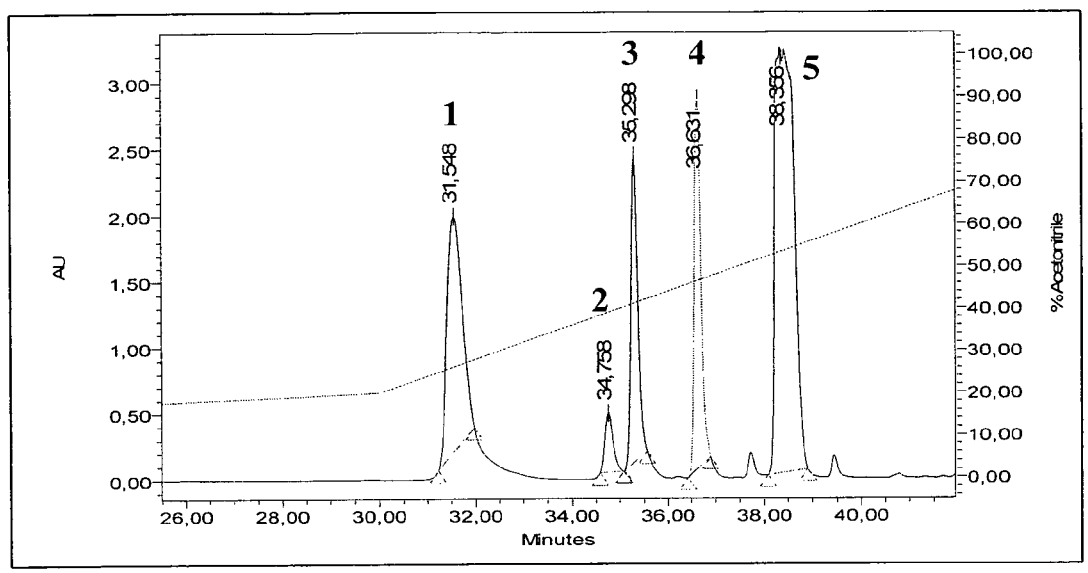

MICROBIOLOGICAL METHOD FOR SYNTHESIZING CINNAMOYL AMIDE DERIVATIVES OF AMINO ACIDS

CROSS-REFERENCE TO RELATED APPLICATIONS

The present application is a National Stage Application of PCT/FR2009/000662, filed Jun. 5, 2009, which claims priority to French Patent Application No. 08 03188, filed Jun. 9, 2008, which are both incorporated herein by reference in their entireties.

FIELD OF THE INVENTION

The invention relates to a method for the microbiological production of cinnamoyl amide derivatives of amino acids, certain products that result therefrom and uses thereof, notably as antioxidants.

BACKGROUND OF THE INVENTION

Molecules of this family have essentially been isolated from the vegetable kingdom, principally in the reproductive system of plants, whereas they appear to be absent from the green parts of plants (Martin-Tanguy et al., *Phytochemistry*, 17: 1927-1928, 1978; *FEBS Lett.*, 108: 176-178, 1979). In 2003, Alemano et al. (*Annals of Botany*, 92: 613-623) identified N-caffeoyl-tyrosine and N-caffeoyl-DOPA in the somatic embryogenesis cells of *Theobroma cacao*. Later, in grains of green coffee (robusta), p-coumaroyl-N-tyrosine, feruloyl-N-tyrosine, feruloyl-N-tryptophan and caffeoyl-N-phenylalanine were identified (Clifford and Knight, *Food chemistry*, 87: 457-453, 2003), whereas their antioxidant capacity had already been found previously (Sanbongi et al., *J. Agric. Food Chem.* 46: 454-457, 1998). Then, Stark and Hoffman (*J. Agric. Food Chem.*, 53: 5419-5428, 2005) and then Stark et al. (*J. Agric. Food Chem.*, 54: 2859-2867, 2006) identified and completed the list with other analogs present in the same vegetable sources.

The amides of cinnamic and hydroxycinnamic acids have in particular been listed and evaluated for their important antioxidant activities (Spasova et al., *J. Peptide Sci.*, 12: 369-375, 2006), a property that seems inherent to any structure of this type.

Other molecules such as 4-hydroxycinnamoyl-(L-phenylalanine methyl ester) amide or 3,4-dihydroxycinnamoyl-(L-aspartic acid dibenzyl ester) amide have been cited for their antioxidant activity against oxidation of LDLs (low-density lipoproteins) by copper, and at the same time these molecules inhibit the activity of human acyl-CoA:cholesterol acyltransferase (Lee et al., *Biorg. Med. Chem. Letters*, 14: 4677-4681, 2004); they are therefore implicated in hypercholesterolemia. The N-cinnamoyl amides have also been described as antiplatelet agents (Hung et al., *Bioorganic and Medicinal Chemistry*, 13: 1791-1797, 2005). The clovamides (N-cinnamoyl tyrosine), which are phytoalexins that accumulate in plants following an attack by pathogens (Yamamoto et al., *Pharmacol Biochem Behav*, 40: 465-469, 1991), also belong to this group, and in this connection are known to be powerful antimicrobials.

Finally, vaso-relaxing activities of N-caffeoylamino R acid derivatives (R=GABA or hexanoic acid) have also been described recently (Iizuka et al., *Yakugaku Zasshi*, 123: 963-971, 2003).

The cinnamoyl amide derivatives of amino acids therefore constitute a family of molecules with considerable potential both in the therapeutic and in the cosmetic field, or as preservatives. However, their isolation from plants is difficult, the yields and the amounts are low, and the structures have little diversification.

Methods for the synthesis of certain of these molecules by the chemical route have been described; but they require several stages, use toxic compounds and in consequence are difficult to industrialize:

In the synthesis described by Iizuka et al. (*Yakugaku Zasshi*, 123: 963-971, 2003), four stages are necessary: (1) protection of the hydroxyl functions of the ring by ethyl chloro-acetate in a basic medium, (2) then coupling by dicyclohexylcarbodiimide (DCCDI); (3) the amino acid is then coupled in the presence of triethylamine, and finally (4) a hydrolysis liberates the hydroxyl functions from the aromatic nucleus (deprotection). N-caffeoylglycine, N-cinnamoylglycine, N-caffeoyl-β-alanine, and N-cinnamoyl-β-alanine were synthesized by this method.

Another quicker synthesis is based on fixation of the amino acid (L-aspartic acid or L-tryptophan in this case) on the corresponding acyl chloride after prior protection of the hydroxyl groups of the aromatic ring by dimethylaminopyridine (DMAP). The amidation reaction is carried out by reflux in the presence of tetrahydrofuran (THF), followed finally by deprotection to liberate the hydroxyls (Stark and Hofmann, *J. Agric. Food Chem.*, 53: 5419-5428, 2005; Stark et al., *J. Agric. Food Chem.*, 54: 2859-2867, 2006).

We may also cite the works of Tada et al. (*J. Oleo Sci.*, 51: 19-27, 2002), which describe the synthesis of various derivatives including the methyl ester of N-caffeoyl-O-acetylserine which has strong antioxidant and tyrosinase-inhibiting activity. Moreover, Lee et al. (*Bioorg Med. Chem. Lett.*, 14: 4677-4681, 2004) carried out the synthesis of esters of p-coumaroyl amide of aspartic acid (methyl ester) and of phenylalanine (dibenzyl ester) respectively, by a method equivalent to Iizuka et al. (*Yakugaku Zasshi*, 123: 963-971, 2003) (see above).

There was therefore still a need for a simple method, easy to apply, industrializable, permitting the preparation of cinnamoyl amide derivatives of amino acids.

BRIEF DESCRIPTION OF THE DRAWING

FIG. 1 is an HPLC chromatogram of N-cinnamoyl amide compounds obtained from a culture performed on yeast extract.

DETAILED DESCRIPTION OF THE INVENTION

The first object of the invention is a method of preparing molecules corresponding to the following formula (I):

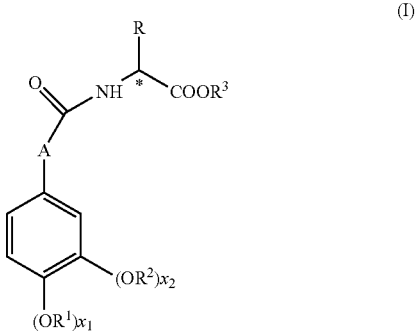

in which:

A represents a group selected from —CH═CH— and —CH$_2$—CH$_2$—, $x_1$ is an integer selected from 0 and 1, $x_2$ is an integer selected from 0 and 1, $R^1$, $R^2$, independently of one another, represent a group selected from: H, $C_1$-$C_6$ alkyls, phenyl, benzyl, the groups —CO—$R^4$, $R^4$ representing a group selected from: $C_1$-$C_6$ alkyls, phenyl, benzyl, $R^3$ represents a group selected from: H, $C_1$-$C_6$ alkyls, phenyl, benzyl, a peptide chain of amino acids comprising 1 to 30 amino acids,

* represents the optical configuration L or D of the amino acid —NH—CHR—COO—, * can represent one or other of the configurations depending on the choice of R, R represents an amino acid side chain selected from: —H (glycine), —$CH_3$ (L-alanine, D-alanine), —$CH_2OH$ (L-serine), —CHOH—$CH_3$ (L-threonine), —$CH_2OR^5$ (L-serine protected on its hydroxyl function), —$CHOR^5$—$CH_3$ (L-threonine protected on its hydroxyl function), $R^5$ representing a group selected from: H, $C_1$-$C_6$ alkyls, phenyl, benzyl, the groups —CO—$R^6$, $R^6$ representing a group selected from: $C_1$-$C_6$ alkyls, phenyl, benzyl.

$C_1$-$C_6$ alkyl means an alkyl group, linear, branched or cyclic, comprising 1 to 6 carbon atoms, for example a methyl, ethyl, n-propyl, isopropyl, n-butyl, t-butyl, isobutyl, n-pentyl, n-hexyl group.

According to the invention, the molecules of formula (I) are prepared by a method that comprises at least one stage of culture of at least one bacterium selected from the Bacillaceae, in the presence of at least two substrates selected from those of the following formulas (II) and (III):

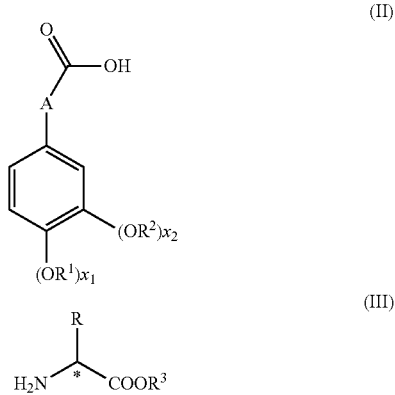

in which A, $x_1$, $x_2$, $R^3$, * and R have the same definition as in formula (I), $R^1$, $R^2$, independently of one another, represent a group selected from: $C_1$-$C_6$ alkyls, phenyl, benzyl, the groups —CO—$R^4$, $R^4$ representing a group selected from: $C_1$-$C_6$ alkyls, phenyl, benzyl.

$C_1$-$C_6$ alkyl means an alkyl group, linear, branched or cyclic, comprising 1 to 6 carbon atoms, for example a methyl, ethyl, n-propyl, isopropyl, n-butyl, t-butyl, isobutyl, n-pentyl, n-hexyl group.

Advantageously, the method of the invention comprises a stage of culture of at least one bacterium selected from those belonging to the genus Bacillus, even more advantageously a bacterium selected from: *Bacillus subtilis, Bacillus licheniformis, Bacillus thermoamylovorans, Bacillus* (or *Geobacillus*) *stearothermophilus, Bacillus caldotenax*.

And preferably, the bacterium is selected from:

*Bacillus subtilis* subsp. *Spizizenii*: DSM 15029 (growth temperature=30° C.)

*Bacillus licheniformis*: DSM 13, ATCC 14580, NCIB 9375 (growth temperature=30° C.)

*Bacillus thermoamylovorans* (strain isolated by the IRD-Marseille laboratory): DSM 13307 (growth temperature=50° C.)

*Bacillus* (or *Geobacillus*) *stearothermophilus*: DSM 22, ATCC 12980, NCIB 8923 (growth temperature=55° C.)

*Bacillus caldotenax*: DSM 406 (growth temperature=70° C.)

Surprisingly, the inventor found that culturing a bacterium described above in the presence of at least one of each of the substrates (II) and (III) gave rise to the formation of an amide bond between the acid function of substrate (II) and amine function of substrate (III) to give access to the corresponding product of formula (I). The method of the invention thus provides access to a family of varied products but nevertheless having very specific structural characteristics connected with the specificity of the bacterium for substrates (II) and (III).

Preferably, in formula (I), one or more of the following conditions are satisfied:

A represents a group —CH=CH—, $R_1$, $R_2$, independently of one another, represent a group selected from: H, —$CH_3$, $R^3$ represents H, R represents an amino acid side chain selected from: —H (glycine), —$CH_3$ (L-alanine, D-alanine), —$CH_2OH$ (L-serine), —CHOH—$CH_3$ (L-threonine).

Appropriate precursors (II) and (III) are selected depending on the way in which compound (I) will be used subsequently:

If the compound of formula (I) has to undergo further stages of synthesis, it may be desirable to prepare it in a protected form, by selecting suitable protective groups $R^1$, $R^2$, $R^3$ and optionally $R^5$.

Notably, when $x_1$=1 or $x_2$=1, for application of the culture stage, we select $R^1 \neq H$, or $R^2 \neq H$, respectively. In fact, the transformation to product (I) is more effective when the aromatic ring of the cinnamoyl derivative (II) does not have a substituent or when the latter are protected. Then it is possible to liberate the hydroxyl functions present on the cinnamoyl ring by enzymatic treatment with a peroxidase (Paice et al., *Applied Environmental Microbiology*, 1993, 59:260-265).

A compound of formula (I) comprising a peptide chain $R^3$ can be obtained directly by the choice of a corresponding substrate (III) in which the peptide chain $R^3$ is already present, or starting from a compound of formula (I) with $R^3$=H by a subsequent stage of grafting on a peptide chain or sequentially by elongation of the amino acid chain (Bodansky, Synthesis, 453-463, 1972).

The compounds of formula (I) with A=-$CH_2$—$CH_2$— can be obtained directly from the corresponding precursor (II) or from a precursor (II) in which A represents —CH=CH— and by working, by means that are well known by a person skilled in the art, by a chemical or microbiological reduction of the double bond (J March, Advanced Organic Chemistry, 1985, Wiley & Sons, 691-700).

When we wish to obtain a single compound of formula (I), it is prepared from two corresponding precursors (II) and (III). It is possible to prepare a mixture of molecules of formula (I) by culture of a bacterium described above in the presence of a mixture of substrates (II) and/or of a mixture of substrates (III).

The bacterium is cultured in a medium which, in addition to compounds (II) and (III), advantageously comprises mineral salts and a yeast extract. Preferably, it comprises the following mineral salts: $KH_2PO_4$, $K_2HPO_4$, NaCl, $NH_4Cl$.

Advantageously, the culture medium contains no other amino acids than those of formula (III), which reduces the stages of purification at the end of the process.

According to another preferred embodiment of the invention, the culture medium also comprises, in addition to the amino acid or amino acids of formula (III), at least one other amino acid selected from: lysine, proline, cysteine. Advantageously, these amino acids are in the (L) form. As the inventor established, these amino acids are not used by the bacterium to participate directly in the formation of a product of formula (I), but they contribute to improving the yield in synthesis of the compounds of formula (I) from amino acids of formula (III) as defined above that are present in the medium. Advantageously, the concentration of one or more of these amino acids in the culture medium is between 1 and 4 mM.

According to the method of the invention, the concentration of the compound of formula (II) in the culture medium is preferably between 0.5 and 10 mM, and advantageously between 1 and 5 mM.

According to the method of the invention, the concentration of the compound of formula (III) in the culture medium is preferably between 0.5 and 20 mM, and advantageously between 2 and 8 mM.

According to the method of the invention, the proportion of the compounds of formula (II) and (III) in mol is: 0.30<(II)/(III)<0.9, preferably 0.40<(II)/(III)<0.8, and advantageously 0.50<(II)/(III)<0.65.

According to one embodiment of the method of the invention, the precursor (II) can be introduced into the culture medium in the form of a vegetable extract. In fact, cinnamic acid is a constituent of certain agricultural wastes and derivatives from the wood industry. It is possible, in the method of the invention, when (II) is cinnamic acid or a derivative of cinnamic acid, to introduce it directly into the culture medium in the form of a composition of agricultural wastes or of effluents from the wood industry. Such products must usually be reprocessed and, thanks to the method of the invention, are thus upgraded.

Preferably, the culture medium is a medium with low content of metals. In particular, the culture medium does not contain iron (notably $Fe^{2+}$ generally supplied by $FeSO_4$ or $FeCl_2$). In fact, it was found that the presence of iron completely inhibited the reaction of formation of (I).

At the end of formation of the compound of formula (I), the presence of which is monitored by HPLC and LC-MS, the product is isolated from the culture medium by a method that advantageously comprises the following stages:
  centrifugation,
  recovery of the supernatant,
  purification of the product (I).

Purification can be done by any means usually employed by a person skilled in the art, such as: liquid-liquid solvent extraction, chromatography, precipitation, crystallization. These means are illustrated more specifically in the experimental section. With the method of the invention it was notably possible to synthesize the following molecules:
  N-cinnamoyl-glycine,
  N-cinnamoyl-L-alanine,
  N-cinnamoyl-D-alanine,
  N-cinnamoyl-L-serine,
  N-cinnamoyl-L-threonine,
  N-(4-methoxycinnamoyl)-glycine,
  N-(4-methoxycinnamoyl)-L-alanine,
  N-(4-methoxycinnamoyl)-D-alanine,
  N-(4-methoxycinnamoyl)-L-serine,
  N-(4-methoxycinnamoyl)-L-threonine,
  N-(3,4-dimethoxycinnamoyl)-glycine,
  N-(3,4-dimethoxycinnamoyl)-L-alanine,
  N-(3,4-dimethoxycinnamoyl)-D-alanine,
  N-(3,4-dimethoxycinnamoyl)-L-serine,
  N-(3,4-dimethoxycinnamoyl)-L-threonine,
  N-coumaroyl-L-threonine,
  N-caffeoyl-L-threonine,
  N-coumaroyl-L-serine,
  N-caffeoyl-L-serine,
  N-coumaroyl-L-alanine,
  N-caffeoyl-L-alanine,
  N-coumaroyl-D-alanine,
  N-caffeoyl-D-alanine,
  N-coumaroyl-glycine,
  N-caffeoyl-glycine.

The invention further relates to a method of manufacture of a medicinal product that comprises at least one stage of culture as was described above to form a compound of formula (I).

Among the molecules of formula (I) obtained by the method of the invention, some are novel and accordingly constitute another object of the invention. Notably, the invention relates to compounds corresponding to formula (Ia) below:

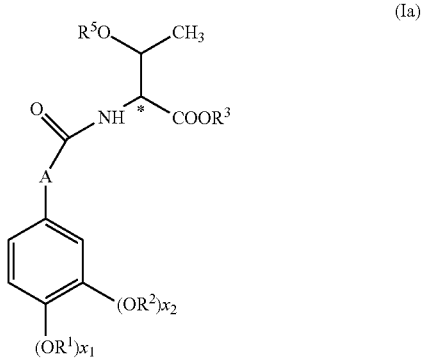

(Ia)

in which:
A represents a group selected from —CH=CH— and —$CH_2$—$CH_2$—,
$x_1$ is an integer selected from 0 and 1,
$x_2$ is an integer selected from 0 and 1,
$R^1$, $R^2$, independently of one another, represent a group selected from: $C_1$-$C_6$ alkyls, phenyl, benzyl, the groups —CO—$R^4$ and $R^4$ represents a group selected from: $C_1$-$C_6$ alkyls, phenyl, benzyl,
$R^3$ represents a group selected from: H, $C_1$-$C_6$ alkyls, phenyl, benzyl, a peptide chain of amino acids comprising 1 to 30 amino acids,
* represents the optical configuration L,
$R^5$ represents a group selected from: H, $C_1$-$C_6$ alkyls, phenyl, benzyl, the groups —CO—$R^6$ and $R^6$ represents a group selected from: $C_1$-$C_5$ alkyls, phenyl, benzyl.

Advantageously, in formula (Ia), one or more of the following conditions are satisfied:
A represents —CH=CH—,
$x_1$ is an integer selected from 0 and 1,
$x_2$ is an integer selected from 0 and 1,
$R^1$, $R^2$, independently of one another, represent a group selected from: H, —$CH_2$,
$R^3$ represents H,
* represents the optical configuration L,
$R^5$ represents H.

Preferably, the compound of formula (Ia) is selected from the following list:
N-cinnamoyl-L-threonine,
N-(4-methoxycinnamoyl)-L-threonine,
N-(3,4-dimethoxycinnamoyl)-L-threonine,
N-caffeoyl-L-threonine.

The invention further relates to the compounds corresponding to formula (Ib) below:

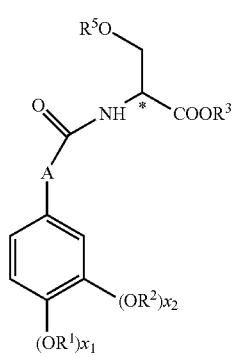

(Ib)

in which:
A represents a group selected from —CH═CH— and —CH$_2$—CH$_2$—,
$x_1$ is an integer selected from 0 and 1,
$x_2$ is an integer selected from 0 and 1,
$R^1$, $R^2$, independently of one another, represent a group selected from: $C_1$-$C_6$ alkyls, phenyl, benzyl, the groups —CO—$R^4$ and $R^4$ represents a group selected from: $C_1$-$C_6$ alkyls, phenyl, benzyl,
$R^3$ represents a group selected from: H, $C_1$-$C_6$ alkyls, phenyl, benzyl, a peptide chain of amino acids comprising 1 to 30 amino acids,
* represents the optical configuration L,
$R^5$ represents a group selected from: H, $C_1$-$C_6$ alkyls, phenyl, benzyl, the groups —CO—$R^6$ and $R^6$ represents a group selected from: $C_1$-$C_6$ alkyls, phenyl, benzyl,
excluding the following compounds:
A represents —CH═CH—, $x_1$=1, $x_2$=1, and
$R^1$=$R^2$=CH$_3$CO—, $R^3$=CH$_3$, $R^5$=CH$_3$CO—, or
$R^1$=$R^2$=CH$_3$CO—, $R^3$=H, $R^5$=H, or
$R^1$=$R^2$=CH$_3$CO—, $R^3$=tBu, $R^5$=tBu.

Advantageously, in formula (Ib) one or more of the following conditions are satisfied:
A represents —CH═CH—,
$x_1$ is an integer selected from 0 and 1,
$x_2$ is an integer selected from 0 and 1,
$R^1$, $R^2$, independently of one another, represent a group selected from: H, CH$_3$,
$R^3$ represents H,
* represents the optical configuration L,
$R^5$ represents H.

Preferably, the compound of formula (Ib) is selected from the following list:
N-cinnamoyl-L-serine,
N-(4-methoxycinnamoyl)-L-serine,
N-(3,4-dimethoxycinnamoyl)-L-serine, The invention further relates to the compounds corresponding to formula (Ic) below:

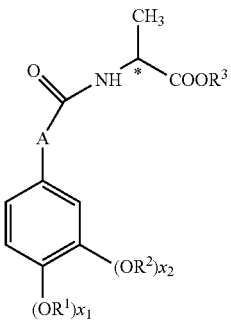

(Ic)

in which:
A represents a group selected from —CH═CH— and —CH$_2$—CH$_2$—,
$x_1$ is an integer selected from 0 and 1,
$x_2$ is an integer selected from 0 and 1,
$R^1$, $R^2$, independently of one another, represent a group selected from: $C_1$-$C_6$ alkyls, phenyl, benzyl, the groups —CO—$R^4$ and $R^4$ represents a group selected from: $C_1$-$C_6$ alkyls, phenyl, benzyl,
$R^3$ represents a group selected from: H, $C_1$-$C_6$ alkyls, phenyl, benzyl, a peptide chain of amino acids comprising 1 to 30 amino acids,
* represents the optical configuration L or D,
excluding cases when:
* represents the optical configuration L and
A represents —CH═CH—, and
$x_1$=$x_2$=0, $R^3$=tBu.

Advantageously, in formula (Ic) one or more of the following conditions are satisfied:
A represents —CH═CH—,
$x_1$ is an integer selected from 0 and 1,
$x_2$ is an integer selected from 0 and 1,
$R^1$, $R^2$, independently of one another, represent a group selected from: H, CH$_3$,
$R^3$ represents H.

Preferably, the compound of formula (Ic) is selected from the following list:
N-cinnamoyl-L-alanine,
N-(4-methoxycinnamoyl)-L-alanine,
N-(3,4-dimethoxycinnamoyl)-L-alanine,
N-caffeoyl-L-alanine,
N-cinnamoyl-D-alanine,
N-(4-methoxycinnamoyl)-D-alanine,
N-(3,4-dimethoxycinnamoyl)-D-alanine,
N-coumaroyl-D-alanine,
N-caffeoyl-D-alanine.

Finally, the invention also relates to compounds corresponding to formula (Id) below:

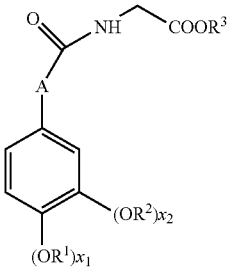

(Id)

in which:
A represents a group selected from —CH═CH— and —CH$_2$—CH$_2$—,
$x_1$ is an integer selected from 0 and 1, $x_2$ is an integer selected from 0 and 1, $R^1$, $R^2$, independently of one another, represent a group selected from: $C_1$-$C_6$ alkyls, phenyl, benzyl, the groups —CO—$R^4$ and $R^4$ represents a group selected from: $C_1$-$C_6$ alkyls, phenyl, benzyl, $R^3$ represents a group selected from: H, $C_1$-$C_6$ alkyls, phenyl, benzyl, a peptide chain of amino acids comprising 1 to 30 amino acids, excluding cases when:
A represents —CH=CH— and:
$x_1$=1, $x_2$=0, $R^1$=$CH_3$, $R^3$=H, or
$x_1$=1, $x_2$=0, $R^1$=$CH_3$, $R^3$=$C_2H_5$, or
$x_1$=$x_2$=0, $R^3$=H.

Advantageously, in formula (Id) one or more of the following conditions are satisfied:

A represents —CH=CH—,
$x_1$ is an integer selected from 0 and 1,
$x_2$ is an integer selected from 0 and 1,
$R^1$, $R^2$, independently of one another, represent a group selected from: H, $CH_3$,
$R^3$ represents H.

Preferably, the compound of formula (Id) is selected from the following list:

N-(3,4-dimethoxycinnamoyl) glycine.

The compounds of the invention have antioxidant and antimicrobial activity. They are capable of acting on the platelets-leukocytes interaction and as anti-inflammatories. They can be used in numerous applications:

In pharmacy, together with a pharmaceutical vehicle, for preparing therapeutic compositions intended for the prevention or treatment of the following pathologies: cancer; inflammatory diseases; cardiovascular diseases such as atherosclerosis, myocardial infarction, cerebrovascular accident, hypercholesterolemia; infectious diseases such as infections due to viruses for example.

In cosmetics, together with a cosmetic vehicle, as preservative, as antiaging agent, as depigmenting agent for the skin and its appendages.

In the food industry as well, the compounds of the invention can be used as preservatives in numerous applications.

I. EXPERIMENTAL SECTION 1.1 Conditions for culture of the bacterium 1.1.1 Bacterial strain Bacterial strain used: *Bacillus subtilis* subsp. *subtilis*.

Morphology and physiology of the bacterium: Straight rods (0.5-2.5×1.2-10 microns) isolated or in chains of varying length, with very resistant single spore. Gram staining is positive, especially at the start of growth; it can also be negative. Mobile by peritrichous flagella. Aerobes or facultative anaerobes. Catalase present. Oxidase positive or negative. Chemo-organotrophs, prototrophs to auxotrophs requiring several growth factors. The peptidoglycan of the wall is of the meso-diaminopimelic acid type. The dominant phospholipids are phosphatidylethanolamine and phosphatidylglygerol. Spore formation is a multiphase process comprising seven successive stages. Ending of dormancy involves three sequential processes: activation, germination and growth. Numerous genetic studies have been conducted on *B. subtilis*, which is the typical species of the genus; more than 355 genes have been localized on the chromosomal map. Owing to the extreme resistance of their spore, the *Bacilli* are ubiquitous. Their primary habitat is the soil, where they play an important role in the carbon and nitrogen cycles. They may also contaminate foodstuffs.

Collection numbers: DSM No. 10, NCIB 3610, ATCC 6051 (DSMZ, Deutsche Sammlung von Mikroorganismen and Zellkulturen, Brunswick, Germany; NCIB, National Center for Biotechnology Information; ATCC, The Global Bioresource center).

Bibliographical Reference: Nakamura et al., *Int. J. Syst. Bacteriol.*, 49:1211-1215, 1999.

1.1.2 Culture Media

The molecules are synthesized by culture of the bacterium. Tests were conducted with a medium lacking iron, in comparison with culture performed in the same conditions but in the presence of iron. The culture media used are as follows:

Medium 1. It contains per liter: $KH_2PO_4$ 0.5 g, $K_2HPO_4$ 0.5 g, NaCl 0.4 g, $NH_4Cl$ 0.4 g, yeast extract (YE, from PANREAC (France), reference 403687.1210) 2 g. The pH is adjusted to 7.0 with 10M KOH solution. Then the medium is autoclaved at 120° C. for 20 min. Routinely, 25 mL cultures are performed in 50 mL conical flasks.

Medium 2. This is identical to medium 1 except for the yeast extract, which is replaced with Yeast Nitrogen Basal (YNB, from DIFCO (France), reference 233520), which does not contain amino acids or ammonium sulfate.

1.1.3 Preparation of the Precursors (II) and (III) and of the Yeast Extract

Compounds (II) were prepared in anaerobiosis (Hungate, 1969. In: Methods in Microbiology, pp. 117-132. Edited by Norris, J. R. & Ribbons, D. W. London: Academic Press), sterilized by filtration (Millipore filter, porosity 0.22 μm), and stored in penicillin bottles under $N_2$ at room temperature and protected from the light (bottles covered with aluminum foil).

The parent solutions of acidic compounds (II) were prepared at a concentration of 250 mM, and were neutralized to pH 7 with soda (0.4 g of tablets to 25 mL of parent solution). The following compounds (II) were tested: cinnamic acid, 4-methoxycinnamic acid, 3,4-dimethoxycinnamic acid.

The parent solutions of compounds (III) are prepared in the same conditions as compounds (II) but at a concentration of 50 mM. The following compounds (III) were tested: glycine, L-alanine, D-alanine, L-serine, D-serine, L-threonine, D-threonine, L-valine, D-valine, L-leucine, D-leucine, L-isoleucine, D-isoleucine, L-phenylalanine, D-phenylalanine, L-tyrosine, D-tyrosine, L-aspartic acid, D-aspartic acid, L-glutamic acid, D-glutamic acid, L-asparagine, D-asparagine, L-glutamine, D-glutamine, L-cysteine, D-cysteine, L-histidine, D-histidine, L-lysine, D-lysine, L-methionine, D-methionine, L-proline, D-proline, L-tryptophan, D-tryptophan. The compounds of formula (III) were tested either separately using a culture medium lacking amino acids (i.e. with YNB as yeast extract), or mixed.

The parent solutions of the yeast extracts YE [25% (w/v)] (yeast extract from FLUKA, Reference 70161) and YNB (yeast nitrogen base (YNB) also from DIFCO, Reference 233520) are prepared and sterilized in the autoclave for 20 min at 121° C.

1.1.4 Culture Conditions for the Usual Production of a Single Metabolite

The strain is first thawed, then seeded in medium 2 containing 1 mM of substrate (II) (preculture). After 24 h at 30° C. in INFORS incubators, with stirring at 150 rev/min, the cultures are inoculated with 10% (v/v) of the preculture in medium 2 containing 1 mM of aromatic substrate (II) and 2 mM of amino acid (III). The cultures are finally stirred in the same conditions for 48 h.

Culture volume(s): the experiments were performed starting with cultures of 25 ml or of 1 liter, in 50 mL conical flasks or cotton-plugged 2L bottles, respectively.

1.2 Extraction, Purification and Identification of the Compounds 1.2.1 Extraction, Purification After centrifugation of the 25 mL culture, the supernatant is acidified with a few drops of glacial acetic acid or formic acid to a final pH of 2, then extracted 3 times with ethyl acetate in a separatory funnel. After the organic phase has been evaporated to dryness, two routes are possible:

Firstly, it is possible to keep this dry fraction, which contains about 90-95% of the desired compound. Testing by HPLC is performed in this case by taking up the dry extract in methanol and injecting 10 μl in a reversed-phase HPLC system.

Secondly, the dry extract is taken up in acidified water (1% HCOOH), and is deposited on a SePack $C_{18}$ cartridge (WATERS, France) which is rinsed with 10-15 ml of acidified water (1% HCOOH). The molecule is then eluted with pure methanol, the eluate is evaporated in a BUCHI rotary evaporator under vacuum and the solid obtained is put in a pill machine. The compounds can easily be stored at room temperature or at 4° C. in the solid form, or at −20° C. in liquid form in methanol.

In the case of 1-liter cultures, the dry residue obtained after the stage of extraction with ethyl acetate is taken up in acidified water with 1% of formic acid and then deposited on a LICHROPREP RP18 column (Merck, Ref. 1.09303.0100, volume of the phase 7 ml). This is then rinsed with 3 volumes of acidified water (1% HCOOH), and the compounds are finally eluted with pure methanol; after evaporation, the solid is recovered in a bottle and weighed.

1.2.2 Routine Testing by HPLC

After taking 1 ml of bacterial culture and after centrifugation (8000 g, 5 min), 400 μL of supernatant is acidified with 20 μL of glacial acetic acid and then centrifuged again (precipitation of extracellular proteins). Finally, 10 to 20 μL of the supernatant obtained is injected into the HPLC system. Analysis and testing can also be carried out on the pure molecule obtained above.

The HPLC analyses are carried out on a WATERS instrument equipped with a membrane degasser, a RHEODYNE 7725i injector (La Jola, USA), a binary pump 1525, a thermostatic furnace and a diode array detector 2996. The equipment is controlled by Millenium 32 software, version 4.0. Separation is provided by a SYMMETRY $C_{18}$ column (150× 4.6 mm, porosity 5 μm, WATERS). The mobile phase, supplied at a flow of 0.8 mL/min, is composed of two solvents: acetonitrile (A) and distilled water acidified with 1% of acetic acid (B). The total elution time is 55 min. The gradient used has three stages:

Stage 1: from 5 to 20% of A in B for 30 min;
Stage 2: from 20 to 100% of A in B for 20 min;
Stage 3: return to 5% of A in B in 5 min.

The compounds are identified, on the one hand, by determination of the retention time and, on the other hand, from the UV/VIS spectra determined for each compound. Pure molecules were prepared beforehand and serve as standards for HPLC (retention time) and for spectroscopy (UV/VIS, LC-MS, GC-MS).

1.2.3 Identification by LC-MS (HPLC Coupled to Mass Spectrometry)

The HPLC is an HP 1100 chromatograph (AGILENT TECHNOLOGIES, France). Separation is provided by a $C_{18}$ SYMMETRY column (Waters, France), of dimensions 4.6× 250 mm, and with porosity of 5 μm. The system is equipped with an automatic injector, a membrane degasser, a furnace and a mono-variable wavelength detector. The mass spectrometer used is an instrument from APPLIED BIOSYSTEMS (France), model SCIEX Api150EX, which uses the electrospray ionization mode. Elution, and data acquisition and processing are provided respectively by the software packages CHEMSTATION and MASSCHROM version 1.1.

Operating conditions: Flow 0.3 ml/min; furnace temperature 30° C.; wavelength (λmax) fixed at 278 nm in the case when compound (II) is not branched in position 3 or 4 of the ring ($x_1=x_2=0$); wavelength (λmax) fixed at 310 nm in other cases. The mobile phase is formed by a gradient of two solvents: $H_2O$ milli-Q acidified with formic acid at 1% (solvent A) and pure acetonitrile (solvent B). The gradient used comprises the following: stage 1, from 5 to 30% of B for 60 min; stage 2: from 30 to 100% of B for 30 min (total time 90 min).

The mass conditions are as follows: values of m/z from 30 to 3000 amu (atomic mass unit), acquisition time 15 ms/scan, cone voltage 20 or 60 Volts, voltage of capillary 4500 Volts, in positive and negative mode, atomizer pressure 45 psi.

1.2.4 Identification by GC-MS (Gas Chromatography Coupled to Mass Spectrometry)

First, the purified solid compound or a dry extract containing a mixture of compounds is submitted to a reaction of derivation by BSTFA+TMCS or of methyl esterification.

Derivation

The reactions take place in a 2-ml CHROMACOL tube sealed with a stopper and a hermetic septum. Two types of derivation were carried out in this work:

Trimethylsilylation with BSTFA containing a catalyst: This technique is used for aromatic compounds when the derivation reaction is more difficult, the catalyst being in this case TMCS (trimethylchlorosilane). 100 μL of pyridine and 100 μL of BSTFA reagent containing 1% of TMCS (trimethylchlorosilane) (from SIGMA-ALDRICH, reference T6381) are added to 0.3-1 mg of sample. The solution is stoved for 15 to 20 min at 60° C. It is then evaporated under nitrogen and the dry residue is taken up in methanol or ethyl acetate (100 to 500 μL) for GC-MS analysis.

Methyl esterification: This method was developed specifically for the N-cinnamoyl amide compounds of amino acids. 100 μL of PFPA (pentafluoropropionic anhydride, SIGMA-ALDRICH No. 394904) is added to about 0.3-1 mg of sample dissolved in 100 μL of methanol. The solution obtained is then stoved for 30 min at 60° C. The PFPA is evaporated under nitrogen and the dry residue is taken up in ethyl acetate (100 to 500 μL) for GC-MS analysis.

Analyses

The analyses were carried out with a GC-MS instrument (AGILENT TECHNOLOGIES) composed of a 6890N GC system chromatograph, a 5973 Mass Selectiv Detector mass spectrometer equipped with an electron impact ion source and an analyzer of the quadrupole type, acquisition software MSD-CHEMSTATION as well as databases (NIST, WILEY). The compounds are separated by means of a DB-1MS capillary column (30 m×0.25 mm, from JW Scientific) with temperature limits between −60° C. and 350° C. The mobile phase is helium. The column pressure is 10.5 psi and the flow is 1 mL/min. The injector temperature (Inlet) is 280° C. The programming of the temperature gradient is as follows: 1 min at 100° C., then increasing from 100 to 260° C. at a rate of 4°/min, then 10 min at 260° C. The total elution time is 51 min. The aromatic compounds are submitted to derivation beforehand to make them more volatile.

II. RESULTS

2.1 Figure

FIG. 1. HPLC chromatogram of the N-cinnamoyl amide compounds obtained from a culture performed on yeast extract. Culture of 25 mL performed in medium 1. 1, 4-methoxy-N-cinnamoyl-L-serine acid; 2, 4-methoxy-N-cinnamoylglycine acid; 3, 4-methoxy-N-cinnamoyl-L-threonine acid; 4, 4-methoxy-N-cinnamoyl-(D,L)-alanine acid; 5, 4-methoxycinnamic acid, residual substrate in the culture.

2.2 Molecules Synthesized from Medium 1

Medium 1 contains yeast extract; there is no additional supply of amino acids in this medium, the yeast extract contains them already. When the bacterium grows in this medium in the presence of cinnamic acid, or of 4-methoxycinnamic acid, or of 3,4-dimethoxycinnamic acid, it produces N-cinnamoyl amides of amino acids only when this medium is free from iron, i.e. in the conditions described in the experimental section. In fact, there is no synthesis of molecules of the N-cinnamoyl amide type in the presence of iron (0.3 mg/L added to the medium), based on analysis by HPLC and inspection of the chemical structures by LC-MS and GC-MS.

Extraction of the supernatant acidified with ethyl acetate and analysis of the molecules in LC-MS enabled us to clearly demonstrate 5 molecules (FIG. 1). Thus, L-serine, L-threonine, L- or D-alanine supplied by the culture medium are condensed with the precursor (II) to form the acids 4-methoxy-N-cinnamoyl-L-serine, 4-methoxy-N-cinnamoyl-L-threonine, 4-methoxy-N-cinnamoyl-L-alanine and 4-methoxy-N-cinnamoyl-D-alanine. The enzyme makes no difference between the two forms L and D of alanine. A small amount of the acid 4-methoxy-N-cinnamoyl-glycine was also obtained.

Using cinnamic acid or 3,4-dimethoxycinnamic acid for compound (II), the corresponding molecules are obtained in the same way for each substrate (amide derivatives of L-serine, L-threonine, L-alanine and D-alanine, glycine).

After hydrolysis of the amide bond by reflux in the presence of $H_2SO_4$ for 6 hours, extraction of the solution with ethyl acetate and evaporation of the aqueous phase to dryness, GC-MS analysis after derivation with BSTFA reveals the presence of glycine, serine, threonine and alanine, thus confirming the structures of the molecules.

Conclusions: Formation of the following molecules is observed: 1, 4-methoxy-N-cinnamoylserine acid; 2, 4-methoxy-N-cinnamoylglycine acid; 3, 4-methoxy-N-cinnamoylthreonine acid; 4, 4-methoxy-N-cinnamoylalanine acid. Serine, threonine, alanine and probably glycine are present in the yeast extract YE. One or more enzymes of the bacterium make these amino acids react on the precursor (II) (in this case 4-methoxycinnamic acid), the amino acids being supplied by the yeast extract.

2.3 Cultures Performed with Medium 2 for Targeted Production of a Single Molecule A culture medium (medium 2) lacking amino acids makes it possible to obtain a single molecule at a time, by adding the amino acid (compound (III) in this same medium). In this way, it was possible to determine the stereoselectivity of the reaction with respect to the amino acid (D or L). Four cultures were performed in the presence of YNB (yeast extract containing neither amino acids, nor ammonium sulfate), by adding a single amino acid per culture at a concentration of 2 mM, and in the presence of 4-methoxycinnamic acid at 1 mM. After 72 hours of culture, HPLC analysis shows that, compared with FIG. 1, the aromatic substrate is completely transformed. Moreover, in these conditions, a single N-cinnamoyl amide compound is produced. The spectral and chemical characteristics of N-cinnamoyl amides obtained starting from 4-methoxycinnamic acid are summarized as an example in Table 1 below.

TABLE 1

Characteristics and rate of production of the N-cinnamoyl amide compounds of amino acids obtained by culture of the bacterium in medium 2. Compound (II), 4-methoxycinnamic acid 1 mM; compound (III), the amino acid mentioned here at 2 mM.

| Compound | RT (min)[1] | λmax (nm)[2] | Mass of the methyl ester[3] | Output[4] (mg/L) |
|---|---|---|---|---|
| 4-Methoxycinnamic acid | 38.35 | 307 | 220 | 0 |
| 4-methoxy-N-cinnamoyl-L-serine | 31.96 | 307 | 279 | 198 |
| 4-methoxy-N-cinnamoyl-D-serine | — | — | 279 | 0 |
| 4-methoxy-N-cinnamoyl-L-threonine | 35.26 | 307 | 293 | 176 |
| 4-methoxy-N-cinnamoyl-D-threonine | — | — | 293 | 0 |
| 4-methoxy-N-cinnamoyl-L-alanine | 36.43 | 307 | 263 | 191 |
| 4-methoxy-N-cinnamoyl-D-alanine | 36.44 | 307 | 263 | 173 |
| 4-methoxy-N-cinnamoylglycine | 34.76 | 307 | 249 | ND |

[1]RT, retention time in HPLC determined on a chain (cf. experimental section).
[2]Maximum wavelength of the molecules determined from HPLC analysis.
[3]Calculated mass of the methyl ester. On their own, the derivatives of glycine and of alanine show a molecular ion equivalent to this value in GC-MS; for the derivatives of serine and of threonine, in GC-MS they form an alkene corresponding to the reaction of dehydration of the primary and secondary alcohol function, respectively.
[4]The quantities were determined for 1 liter of culture after 72 h, after extraction of the supernatant with ethyl acetate and purification on the $C_{18}$ chromatographic support (cf. experimental section).
ND, not determined.

2.4 Stereoselectivity of the Enzyme with Respect to the Amino Acid (D or L)

The experiments show that the bacterial enzyme binds L-serine and L-threonine (but not the D form) to the aromatic substrate, whereas it does not differentiate L- or D-alanine. As for glycine, it does not possess an asymmetric carbon (cf. Table 1 as example).

2.5 Relations Between Aromatic Structure and Activity

The enzyme only acts on nonhydroxylated cinnamic compounds. We also tested several aromatic substrates following the same protocol: p-hydroxybenzoic, protocatechuic, cinnamic, p-coumaric, ferulic, 4-methoxycinnamic, 3,4-dimethoxycinnamic, 3,4,5-trimethoxycinnamic acids, and catechol. On their own, cinnamic, 4-methoxycinnamic, and 3,4-dimethoxycinnamic acids were transformed to N-cinnamoylamide derivatives. Thus, two comments may be made:

(1) The synthesis is carried out with compounds with structure equivalent to formula (II).

(2) When a single —OH group is present on the aromatic ring (position 3, 4 or 5), the synthesis no longer goes.

2.6 Rate of Production Starting from 1 Liter of Culture (Medium 2)

A liter of culture (medium 2) containing 2 mM of a single amino acid (selected from: L-alanine, D-alanine, L-serine, L-threonine) and 1 mM of 4-methoxycinnamic acid (compound (II)) is incubated at 30° C. for 72 h (stirring at 150 rev/min). After extraction with ethyl acetate, purification on $C_{18}$ support as described above, and examination of structure by HPLC, LC-MS and GC-MS, the following amounts are obtained (cf. Table 1):

4-methoxy-N-cinnamoyl-L-serine: 198 mg for 1 liter
4-methoxy-N-cinnamoyl-L-threonine: 176 mg for 1 liter
4-methoxy-N-cinnamoyl-L-alanine: 191 mg for 1 liter
4-methoxy-N-cinnamoyl-D-alanine: 173 mg for 1 liter

The invention claimed is:

1. A method of preparing molecules corresponding to formula (I) below:

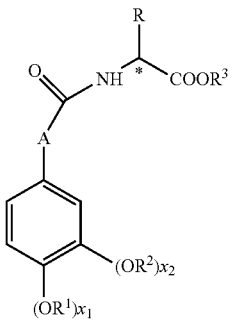

(I)

in which:
A represents a group selected from —CH=CH— and —CH$_2$—CH$_2$—,
$x_1$ is an integer selected from 0 and 1,
$x_2$ is an integer selected from 0 and 1,
$R^1$, $R^2$, independently of one another, represent a group selected from: H, $C_1$-$C_6$ alkyls, phenyl, benzyl, and —CO—$R^4$, and
$R^4$ represents a group selected from: $C_1$-$C_6$ alkyls, phenyl, and benzyl,
$R^3$ represents a group selected from: H, $C_1$-$C_6$ alkyls, phenyl, benzyl, and a peptide chain of amino acids comprising 1 to 30 amino acids,
\* represents the optical configuration L or D of the amino acid —NH—CHR—COO—, \* can represent one or other of the configurations depending on the choice of R,
R represents an amino acid side chain selected from: —H (glycine), —CH$_3$ (L-alanine, D-alanine), —CH$_2$OH (L-serine), —CHOH—CH$_3$ (L-threonine), —CH$_2$OR$^5$ (L-serine protected on its hydroxyl function), and —CHOR$^5$—CH$_3$ (L-threonine protected on its hydroxyl function),
$R^5$ represents a group selected from: H, $C_1$-$C_6$ alkyls, phenyl, benzyl, and —CO—$R^6$, and
$R^6$ represents a group selected from: $C_1$-$C_6$ alkyls, phenyl, and benzyl,
said method comprising at least one stage of culture of at least one bacterium selected from the Bacillaceae, in the presence of at least two substrates selected from those corresponding to formulas (II) and (III) below:

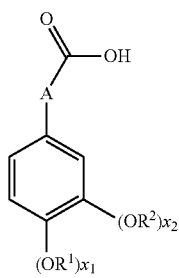

(II)

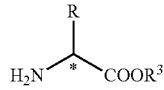

(III)

in which A, $x_1$, $x_2$, $R^3$, \* and R have the same definition as in formula (I),
$R^1$, $R^2$, independently of one another, represent a group selected from: $C_1$-$C_6$ alkyls, phenyl, benzyl, and —CO—$R^4$, and
$R^4$ represents a group selected from: $C_1$-$C_6$ alkyls, phenyl, and benzyl.

2. The method as claimed in claim 1, wherein the bacterium is selected from those belonging to the genus *Bacillus*.

3. The method as claimed in claim 2, wherein the bacterium is selected from: *Bacillus subtilis* subsp. *Spizizenii*: DSM 15029, *Bacillus licheniformis*: DSM 13, ATCC 14580, NCIB 9375, *Bacillus thermoamylovorans*: DSM 13307, *Bacillus stearothermophilus*: DSM 22, ATCC 12980, NCIB 8923, and *Bacillus caldotenax*: DSM 406.

4. The method as claimed in claim 1, wherein in formula (I), one or more of the following conditions are satisfied:
A represents a group —CH=CH—,
$R^1$, $R^2$, independently of one another, represent a group selected from: H, and a methyl group,
$R^3$ represents H, and
R represents an amino acid side chain selected from: —H (glycine), —CH$_3$ (L-alanine, D-alanine), —CH$_2$OH (L-serine), and —CHOH—CH$_3$ (L-threonine).

5. The method as claimed in claim 1, wherein the bacterium is cultured in a medium that comprises mineral salts and a yeast extract.

6. The method as claimed in claim 1, wherein the bacterium is cultured in a medium that comprises, in addition to a substrate or substrates of formula (III), at least one amino acid selected from: lysine, proline, and cysteine.

7. The method as claimed in claim 1, characterized in that a substrate of formula (II) is introduced into the culture medium in the form of a vegetable extract.

8. The method as claimed in claim 1, which further comprises the following stages: centrifugation, recovery of the supernatant, and purification of the molecule of formula (I).

9. The method as claimed in claim 1, wherein the molecule of formula (I) is selected from: N-cinnamoyl-glycine, N-cinnamoyl-L-alanine, N-cinnamoyl-D-alanine, N-cinnamoyl-L-serine, N-cinnamoyl-L-threonine, N-(4-methoxycinnamoyl)-glycine, N-(4-methoxycinnamoyl)-L-alanine, N-(4-methoxycinnamoyl)-D-alanine, N-(4-methoxycinnamoyl)-L-serine, N-(4-methoxycinnamoyl)-L-threonine, N-(3,4-dimethoxycinnamoyl)-glycine, N-(3,4-dimethoxycinnamoyl)-L-alanine, N-(3,4-dimethoxycinnamoyl)-D-alanine, N-(3,4-dimethoxycinnamoyl)-L-serine, N-(3,4-dimethoxycinnamoyl)-L-threonine, N-coumaroyl-L-threonine, N-caffeoyl-L-threonine, N-coumaroyl-L-serine, N-caffeoyl-L-serine, N-coumaroyl-L-alanine, N-caffeoyl-L-alanine, N-coumaroyl-D-alanine, N-caffeoyl-D-alanine, N-coumaroyl-glycine, and N-caffeoyl-glycine.

10. The method as claimed in claim 2, wherein the bacterium is selected from *Bacillus subtilis*, *Bacillus licheniformis*, *Bacillus thermoamylovorans*, *Bacillus stearothermophilus*, and *Bacillus caldotenax*.

\* \* \* \* \*